United States Patent
Qiu et al.

(10) Patent No.: US 8,783,868 B2
(45) Date of Patent: Jul. 22, 2014

(54) TWO-DIMENSIONAL CONFOCAL IMAGING USING OCT LIGHT SOURCE AND SCAN OPTICS

(71) Applicant: Carl Zeiss Meditec, Inc., Dublin, CA (US)

(72) Inventors: Yue Qiu, Pleasanton, CA (US); Hueyming Tzeng, San Jose, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 13/725,264

(22) Filed: Dec. 21, 2012

(65) Prior Publication Data

US 2014/0176903 A1    Jun. 26, 2014

(51) Int. Cl.
  *A61B 3/14* (2006.01)
  *A61B 3/00* (2006.01)

(52) U.S. Cl.
  USPC .................................. 351/206; 351/246

(58) Field of Classification Search
  USPC ................................................ 351/200–246
  See application file for complete search history.

(56) References Cited

U.S. PATENT DOCUMENTS

| | | | |
|---|---|---|---|
| 5,321,501 A * | 6/1994 | Swanson et al. | 356/479 |
| 5,926,592 A | 7/1999 | Harris et al. | |
| 6,769,769 B2 | 8/2004 | Podoleanu et al. | |
| 7,301,644 B2 | 11/2007 | Knighton et al. | |
| 7,382,464 B2 | 6/2008 | Everett et al. | |
| 7,535,577 B2 | 5/2009 | Podoleanu et al. | |
| 7,649,629 B2 * | 1/2010 | Rogers et al. | 356/479 |
| 2008/0088852 A1 | 4/2008 | Rogers et al. | |
| 2010/0321675 A1 | 12/2010 | Huang et al. | |
| 2011/0234978 A1 | 9/2011 | Hammer et al. | |
| 2012/0218558 A1 | 8/2012 | Cenko et al. | |

FOREIGN PATENT DOCUMENTS

| | | |
|---|---|---|
| EP | 2517618 A2 | 10/2012 |
| GB | 2429522 A | 2/2007 |

OTHER PUBLICATIONS

Fujimoto et al., "Optical Coherence Tomography: An Emerging Technology for Biomedical Imaging and Optical Biopsy", Neoplasia, vol. 2, No. 1-2, Jan.-Apr. 2000, pp. 9-25.

Fujimoto, James G., "Optical Coherence Tomography for Ultrahigh Resolution in vivo Imaging", Nature Biotechnology, vol. 21 No. 11, Nov. 2003, pp. 1361-1367.

Hitzenberger et al., "Three-Dimensional Imaging of the Human Retina by High-Speed Optical Coherence Tomography", Optics Express, vol. 11, No. 21, Oct. 20, 2003, pp. 2753-2761.

(Continued)

*Primary Examiner* — Mohammed Hasan
(74) *Attorney, Agent, or Firm* — Morrison & Foerster LLP

(57) ABSTRACT

Various approaches are disclosed for simultaneously generating optical coherence tomography (OCT) and confocal scanning laser images by spatially separating the signal normally used for OCT imaging with selective reflecting or beam directing devices. In one preferred embodiment, the invention includes a mirror having a central transmission region, such that the radially outer region of the returning signal beam is reflected and used for generating a confocal image while the central part of the signal beam is transmitted and used to generate an OCT image. In other embodiments, the signals may be spatially separated in other ways, such as with an optic having a reflective center surface, a mirror having two parts oriented at different angles, one or more wedged optics, or a dispersive component. A further aspect of the invention is the ability to increase the frame rate of the confocal imaging.

12 Claims, 5 Drawing Sheets

(56) References Cited

OTHER PUBLICATIONS

Leitgeb et al., "Ultrahigh Resolution Fourier Domain Optical Coherence Tomography", Optics Express, vol. 12, No. 10, May 17, 2004, pp. 2156-2165.

Podoleanu et al., "Combined Multiplanar Optical Coherence Tomography and Confocal Scanning Ophthalmoscopy", Journal of Biomedical Optics, vol. 9, No. 1, Jan./Feb. 2004, pp. 86-93.

Podoleanu et al., "En-Face Coherence Imaging using Galvanometer Scanner Modulation", Optics Letters, vol. 23, No. 3, Feb. 1, 1998, pp. 147-149.

Podoleanu et al., "Noise Analysis of a Combined Optical Coherence Tomograph and a Confocal Scanning Ophthalmoscope", Applied Optics, vol. 38, No. 10, Apr. 1, 1999, pp. 2116-2127.

Podoleanu et al., "Sequential Optical Coherence Tomography and Confocal Imaging", Optics Letters, vol. 29, No. 4, Feb. 15, 2004, pp. 364-366.

Podoleanu et al., "Simultaneous En-Face Imaging of Two Layers in the Human Retina by Low-Coherence Reflectometry", Optics Letters, vol. 22, No. 13, Jul. 1, 1997, pp. 1039-1041.

Rollins et al., "Emerging Clinical Applications of Optical Coherence Tomography", Optics and Photonics News, vol. 13, No. 4, Apr. 2002, pp. 36-41.

Sharp et al., "The Scanning laser Ophthalmoscope—A Review of its Role in Bioscience and Medicine", Physics in Medicine and Biology, vol. 49, 2004, pp. 1085-1096.

International Search Report and Written Opinion received for PCT Patent Application No. PCT/EP2013/077500, mailed on May 27, 2014, 16 pages.

Podoleanu et al., "Combined Optical Coherence Tomograph and Scanning Laser Ophthalmoscope", Electronics Letters, vol. 34, No. 11, May 28, 1998, pp. 1088-1090.

Podoleanu et al., "Simultaneous OCT/confocal—OCT/ICG System for Imaging the Eye", Proceeding of SPIE, vol. 5578, 2004, pp. 159-166, July \* cited by examiner

TWO-DIMENSIONAL CONFOCAL IMAGING USING OCT LIGHT SOURCE AND SCAN OPTICS

FIELD OF THE INVENTION

This invention relates to optical imaging and diagnostic devices. The invention provides a device to simultaneously record both optical coherence tomography (OCT) images and confocal laser scanning ophthalmoscopy (CLSO) images.

BACKGROUND

In optical imaging of biological tissues, especially the living human eye, it has been shown in recent years that both optical coherence tomography (OCT) and confocal scanning laser imaging systems have particular individual advantages.

Confocal scanning laser imaging has been successfully applied to retinal imaging and is now well accepted by ophthalmologists in imaging the anatomic structures of the retina (see for example, Sharp, P. F. et al. (2004). "The scanning laser ophthalmoscope—a review of its role in bioscience and medicine." Physics in Medicine and Biology 49(7): 1085-1096). The depth resolution of a confocal scanning laser ophthalmoscope (CSLO) is determined by the depth of focus of the confocal optics, and as a result, it typically has an axial resolution of approximately 300 microns.

In contrast to CSLO, the axial resolution of OCT is determined by the coherence length of the light source used, and thus can provide a much higher axial imaging resolution—on the order of 10 microns. OCT is particularly useful for diagnostics that require high depth resolution tomographic imaging (Fujimoto, J. G. et al. (2000). "Optical coherence tomography: an emerging technology for biomedical imaging and optical biopsy." Neoplasia 2(1-2): 9-25; Rollins, A. M. et al. (2002). "Emerging clinical applications of optical coherence tomography." Optics and Photonics News 13(4): 36-41; Fujimoto, J. G. (2003). "Optical coherence tomography for ultrahigh resolution in vivo imaging." Nature Biotechnology 21(11): 1361-1367).

Although OCT measures optical reflectivity over a volume of interest, attempts have been made to use the data to produce en-face images that look like the retinal images from an ophthalmoscope (Podoleanu, A. G. et al. (1997). "Simultaneous en-face imaging of two layers in the human retina by low-coherence reflectometry." Optics Letters 22(13): 1039-1041; Podoleanu, A. G. et al. (1998). "En-face coherence imaging using galvanometer scanner modulation." Optics Letters 23(3): 147-149). In principle, OCT can be used to measure optical reflectivity at a dense set of points covering a volume of interest, and then the OCT data can be reduced to simulate the en-face image that would be seen by a CSLO or other ophthalmoscope. In one approach, the OCT signal is used to simultaneously create, in addition to an OCT image, an anatomic structure image with an appearance similar to that of a CSLO image. This can be done by integrating, or superimposing on top of one another, multiple OCT signals along the depth dimension. The result is an en-face image based on the averaged overall depth reflectivity for each transverse pixel (Hitzenberger, C. K. et al. (2003). "Three-dimensional imaging of the human retina by high-speed optical coherence tomography." Optics Express 11(21): 2753-2761). Another approach to generating a CSLO-like image uses multiple light sources of different coherence lengths. This allows simultaneous generation of multiple OCT images of different depth resolutions. Still another approach uses low-pass electronic filtering of the OCT signal to extract a CSLO-like image.

However, these en-face images generated from OCT data have a number of drawbacks. In particular, the image quality is typically inferior to traditional confocal images. OCT collection optics generally collect less of the light returning from the sample than CSLO collection optics. As is well known in the art, OCT is an interference-based technique, so only light that is spatially coherent contributes to the signal. The light returning from the sample is also often collected in a single-mode optical fiber. Reflected light that does not couple into that single mode, either because it falls outside the fiber core or because it enters at too steep an angle, is rejected. Often the vast majority of the light reflected from the sample is rejected in this way. In addition, the frame rate of such en-face images is generally constrained by the speed of the OCT scanning optics.

Given these drawbacks of en-face images generated from OCT data and the different advantages of OCT and CSLO, it is desirable to simultaneously generate both OCT and CSLO images. One of the major benefits of combining OCT and CSLO is that they have different depth ranges. Another is that a 2-D image of the sample generated by CSLO can be used to correctly position the OCT system relative to the sample.

Most designs that have been used to generate both OCT and 2-D images of a sample add an additional optical path to an OCT system to support an independent fundus camera, CSLO, line scanning laser ophthalmoscope (LSLO), or similar imaging modality. Nevertheless, attempts have been made to directly use an OCT configuration to generate both an OCT image and a CSLO image. In one approach, the reference light of an OCT interferometer was alternately temporarily blocked to generate a CSLO signal and restored to generate an OCT signal. However, this approach results in sequential, rather than simultaneous, acquisition of the OCT and CSLO images.

Such a technique, which directly uses the OCT configuration to generate both an OCT image and a CSLO image, collects light for both the OCT and the CSLO images through a small pin-hole defined by the core size of a single-mode fiber. The pinhole is on the order of 10 microns. In contrast, the standard pinhole size in a CSLO system is approximately 100 microns. The numerical aperture (NA) is thus much smaller than in a standard CSLO system, resulting in a lower signal-to-noise ratio for a CSLO image generated with an OCT system. Another problem associated with this approach is that the fiber end can strongly reflect the light returning from the sample. The reflected light can be sent to the confocal detector with a strength greater than the light not reflected from the fiber returning from the sample, causing the CSLO sample signal to be overwhelmed by the fiber end reflection.

A second approach that has been used to generate both OCT and CSLO images is to separate the light returned from the sample into two components using a plate beam-splitter. One of the components is used to generate the OCT image, and the other is directed to a separate pinhole and used to generate a CSLO image. Such a design has some advantages over the alternating generation of OCT and CSLO images described above. Because the light used to generate the CSLO image is directed through a separate pinhole, the size of the pinhole can be chosen to optimize the CSLO signal-to-noise ratio. Further, because the light used to generate the CSLO image is not directed toward the single-mode fiber, the CSLO signal is not overwhelmed by reflection from the fiber end. This approach also allows for simultaneous generation of OCT and CSLO images. Finally, this approach allows the same transverse scanner to be used for both the OCT beam and the CSLO beam. Registration between the OCT and confocal images can be achieved with optical alignment of the respective detectors and the free-space beam splitter.

However, this second approach, too, has significant limitations. Because a portion of the returned sample beam is deflected to the CSLO pinhole, the OCT signal strength is reduced. It also does not maximize the signal to the CSLO detector because the cladding of the OCT single mode fiber absorbs a significant amount of the returned sample beam that could have been used for the CSLO image.

In U.S. Pat. No. 7,382,464, a novel dual-waveguiding module is disclosed for efficient collection and separation of OCT and CSLO signals. The two signals are separated by channeling most of the multi-mode guided optical power to a CSLO detector. The non-tapped single-mode guided optical wave is further sent to a pure single-mode fiber of a standard OCT system for OCT image generation. That invention achieves highly efficient optical power usage and hence high signal to noise ratio, together with inherent pixel-to-pixel registration of the OCT and CSLO images, and a cost reduction of the combined OCT/CSLO system. A specialized fiber optic is required for this approach.

Here we present another approach to generating simultaneous high quality OCT and CSLO images without use of this specialized fiber optic.

SUMMARY

In this invention, normally uncollected OCT signal is used to generate a confocal image of the sample without affecting the OCT functionality by spatially separating the signal with selective reflecting or beam directing devices. A further aspect of the invention is the ability to increase the frame rate of the 2D confocal imaging. In the invention described herein, since the CSLO signal can be recorded independently from the OCT signal, the frame rate of the CSLO images is limited by the galvanometer scanning rates, which is currently about 4× faster than state of the art camera speeds. Raising the scan speed of the conventional scanners to the mechanical and electrical limits results in a faster frame rate for CSLO image generation.

DETAILED DESCRIPTION

Figure 1:
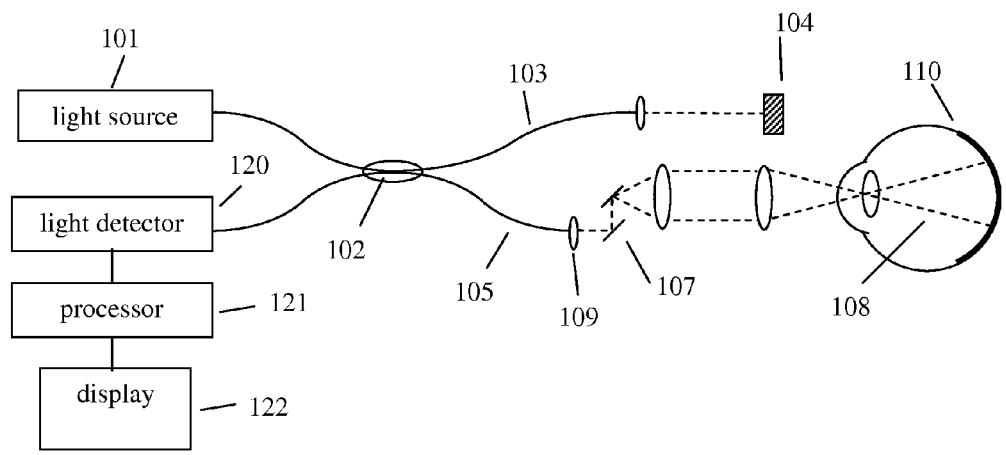
FIG. 1 is a diagram of a generalized frequency-domain OCT system for use in ophthalmology.

A diagram of a generalized frequency-domain OCT (FD-OCT) system for use in ophthalmology is shown in FIG. 1. Light from source 101 is routed, typically by optical fiber 105, to illuminate the sample 110, a typical sample being tissue in the human eye. Typical sources are a broadband light source with short temporal coherence length in the case of spectral-domain OCT (SD-OCT), or a wavelength-tunable laser source in the case of swept-source OCT (SS-OCT). The beam of light (dashed line 108) is scanned laterally (in x and y, if z is parallel to the beam of light) over the area or volume to be imaged, typically with scanning optics 107 between the output of the fiber and the sample. Light backreflected from the sample returns through scanning optics 107 and is collected, typically into the same fiber 105 used to route the light for sample illumination. Lens 109 is used to collimate the illuminating light exiting the fiber and to focus the reflected light back into the fiber for collection. Reference light derived from the same source 101 travels a separate path, in this case involving fiber 103 and retro-reflector 104 with an adjustable optical delay. Those skilled in the art will recognize that a transmissive reference path can also be used and that the adjustable delay could be placed in either the sample or reference arm of the interferometer. Additionally, the interferometer could consist of fiber optics, bulk optical components, or a combination thereof. Collected sample light is combined with reference light, typically in a fiber coupler 102, to form light interference in a detector 120. Although a single fiber port is shown going to the detector, those skilled in the art will recognize that various designs of interferometers can be used for balanced or unbalanced detection of the interference signal. The output from the detector is supplied to a processor 121. The results can be stored in the processor 121 or displayed on display 122.

The interference between the light returning from the sample and from the reference arm causes the intensity of the interfered light to vary across the spectrum. The Fourier transform of the interference light reveals the profile of scattering intensities at different path lengths, and therefore scattering as a function of depth (z-direction) in the sample (see for example Leitgeb, R. et al. (2004). "Ultrahigh resolution Fourier domain optical coherence tomography." Optics Express 12(10): 2156-2165). The scattering profile as a function of depth is called an axial scan (A-scan). A set of A-scans measured at neighboring locations in the sample produces a cross-sectional image (tomogram or B-scan) of the sample. A collection of B-scans makes up a data cube or volume.

Figure 2A:
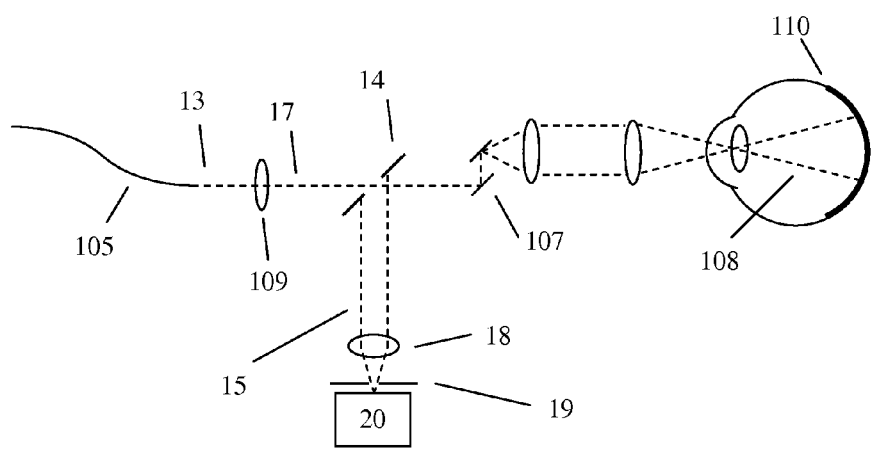
FIG. 2A is a diagram of an embodiment in which a confocal imaging channel is included in the sample arm of an OCT device between the collimating lens and the scanning optics.
Figure 2B:
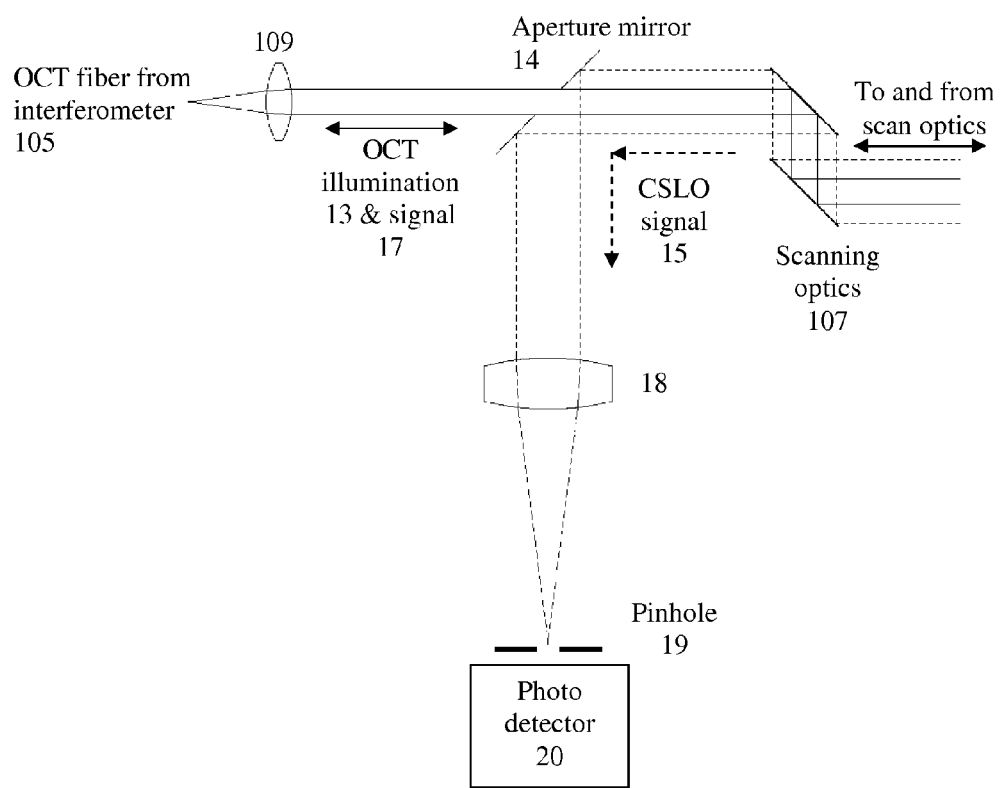
FIG. 2B is a diagram of the same embodiment as in FIG. 2A in the context of the illumination and reflected beam sizes.

FIG. 2A illustrates a preferred embodiment of the present invention in which a confocal imaging channel is included in the sample arm of an OCT device between the collimating lens 109 and the scanning optics 107. The OCT illumination beam 13 exits single mode fiber 105 and is collimated by lens 109. The beam propagates through mirror 14 with a substantially circular aperture aligned with the beam axis, onto the scan mirrors 107, and then towards the sample. When the illumination beam hits the eye and reflects back out of the eye (not shown), the resulting return beam size is defined by the pupil of the patient. This beam size is typically larger than that of the original illumination beam due to the beam diverging. The signal beam propagates back along the same path as the illumination beam, reflecting a second time off of the scan mirrors 107. When the light reaches the mirror 14, the footprint of the signal beam on the mirror 14 is determined by the size of the pupil of the patient, or the size of the scan mirrors, whichever is smaller. The central part of the signal beam 17 will go through the aperture of the mirror 14 and be focused back into the fiber 105 by the collimator 109. The signal that reenters fiber 105 is used to form the OCT image. If the size of the aperture in the mirror 14 is equal to or larger than the illumination beam, the OCT signal is not affected by mirror 14. The outside part of the signal beam 15 will be reflected by mirror 14 onto another lens 18, which will focus the beam onto a photo detector 20 through a pinhole 19. The signal that is detected by the photo detector 20 can be used to form a confocal image. The resulting confocal image may be displayed simultaneously with the OCT image and used, for example, to assist with alignment of the OCT system. FIG. 2B further illustrates this same embodiment in the context of the illumination and reflected beam sizes that allows for spatial separation of the OCT and confocal signals.

The embodiment in FIGS. 2A and 2B is only one embodiment of the present invention. The mirror need not contain an aperture. Instead, it may have any design that has a transmission region aligned with the axis of the returning sample beam, such that a first portion of the light returning from the sample is transmitted through the transmission region and past the mirror, while any portion of the beam radially outside the transmission region is reflected by the mirror. In some embodiments, the transmission region may be a transparent material, which may in some cases have an antireflective coating. In some embodiments the reflecting region is designed to only reflect certain wavelengths of the CSLO signal. After being transmitted through the transmission region, the beam may then be directed through any appropriate set of optics and onto a first detector, from which OCT images data are generated. In some embodiments, as in the preferred embodiment, this may include collimating lens 109 and fiber 105. Any portion of the sample beam that is reflected by the mirror may similarly be directed through any appropriate set of optics and onto a second detector, from which CSLO image data are generated. In some embodiments this may include a focusing lens 18, pinhole 19, and photo detector 20.

In the preferred embodiment, only the light that would not be used to generate OCT data is used to generate CSLO data. Fiber 105, which collects the light used to generate the OCT data, has a limited range of angles over which it can collect light, known as the numerical aperture (NA). Therefore, some outer portions of the returning sample beam are likely to fall outside the range that is collectable by fiber 105. In the embodiment in FIGS. 2A-B, it is this uncollectable light that is reflected by mirror 14 to generated CSLO image data. That is, the transmission region of mirror 14 is of a diameter such that it transmits the portion of the light that can be collected by fiber 105, and it reflects the portion that cannot be collected. The reflected portion of the light can then be used for generation of the CSLO image data. When the mirror is located between the collimating lens and the scan optics, as in the embodiment in FIGS. 2A and 2B, the transmission region diameter that achieves this goal while also maximizing the light going to the CSLO detector is defined by $2*NA*f$, where NA is the numerical aperture of fiber 105, and f is the focal length of lens 109. If the diameter of the transmission region is smaller than this value, the OCT signal will be decreased. If the diameter of the transmission region is larger than this value, the CSLO signal will be decreased.

Figure 2C:
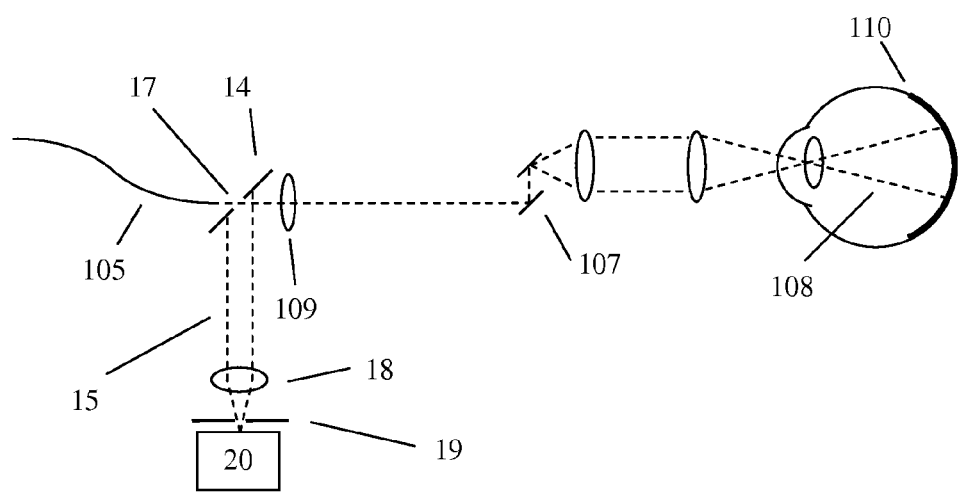
FIG. 2C is a diagram of an embodiment in which a confocal imaging channel is included in the sample arm of an OCT device between the end of the fiber and the collimating lens.

In another embodiment, shown in FIG. 2C, the mirror may instead be located between the end of fiber 105 and the collimating lens 109. In that case, the diameter that will transmit only the light that can be collected by fiber 105 is less than $2*NA*f$. Lens 109 causes the light to converge from lens 109 to the end of fiber 105; therefore, the preferred diameter for the transmission region will depend on where the mirror is located between lens 109 and fiber 105. If the distance between the end of fiber 105 and the transmission region of mirror 14 is defined as s, then the relevant diameter is $2*NA*s$. Similar to the embodiment in FIGS. 2A-B, the transmission region for the embodiment shown in FIG. 2C can be created in various ways, including but not limited to a physical aperture or different transmission coatings. Depending on the optical design of the system, lens 18 may not be required in embodiments where the CSLO signal is separated between the collimating lens 109 and fiber 105, since lens 109 will be focusing the beam.

Figure 3A:
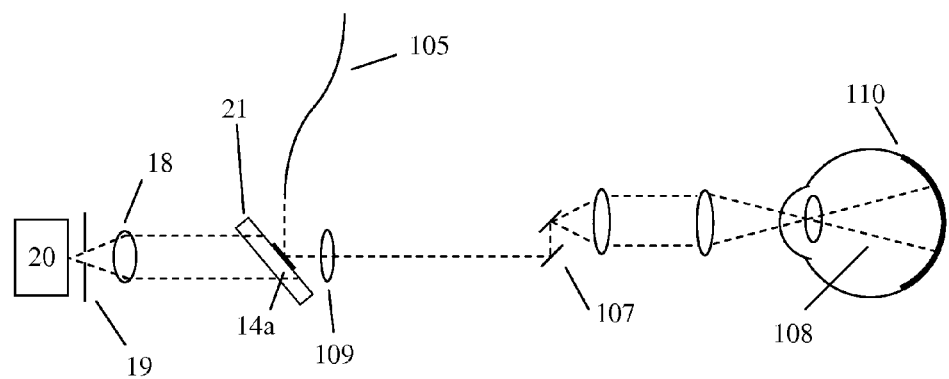
FIG. 3A is a diagram of an embodiment in which the OCT and CSLO signals are spatially decoupled by an optic having a reflective center surface and a surrounding transmission region.

In addition, a mirror having a transmission region aligned with the returning sample beam is also only one possible embodiment by which the signals used for the OCT and CSLO images can be spatially decoupled. For example, as shown in FIG. 3A, instead of a mirror having a transmission region through which the OCT signal is transmitted, there may instead be an optic 21, having a reflective center surface 14a aligned with the axis of the light returning from the sample and a surrounding transmission region that allows for low loss transmission of the CSLO beam. The portion of the returning light reflecting off the reflective center surface 14a is directed toward a detector and used to generate an OCT image. The light surrounding the reflected portion is transmitted through the transmission region and used to generate a CSLO image. The transmission region would preferably be annular, and the surrounding transmission region could have an antireflection coating. In the embodiment shown in FIG. 3A, the optic 21 is located between the collimating lens 109 and the fiber 105. The optic 21 could also be positioned between the collimating lens 109 and the scanning optics 107, similar to the embodiments shown in FIGS. 2A-B. This approach could also be achieved without the surrounding transmission region. That is, a reflective surface may be aligned with the axis of the light returning from the sample to reflect a portion of the returning light toward a detector to generate an OCT image. The light radially surrounding the reflected portion would then be transmitted past the mirror and used to generate a CSLO image.

Figure 3B:
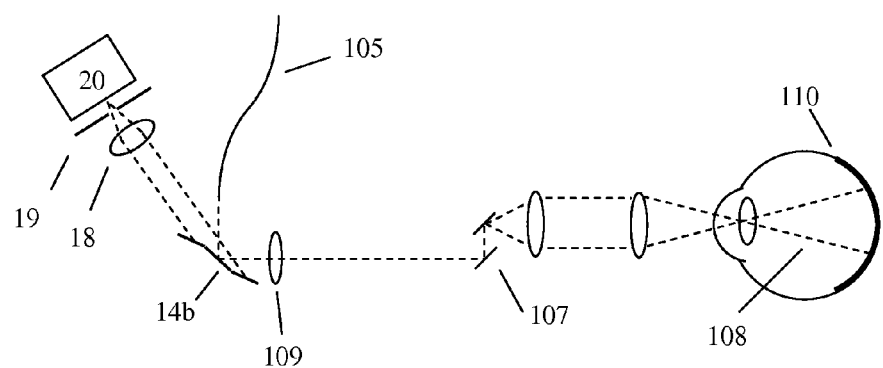
FIG. 3B is a diagram of an embodiment in which the OCT and CSLO signals are spatially decoupled by a mirror having two parts, each oriented at a different angle.
Figure 3C:
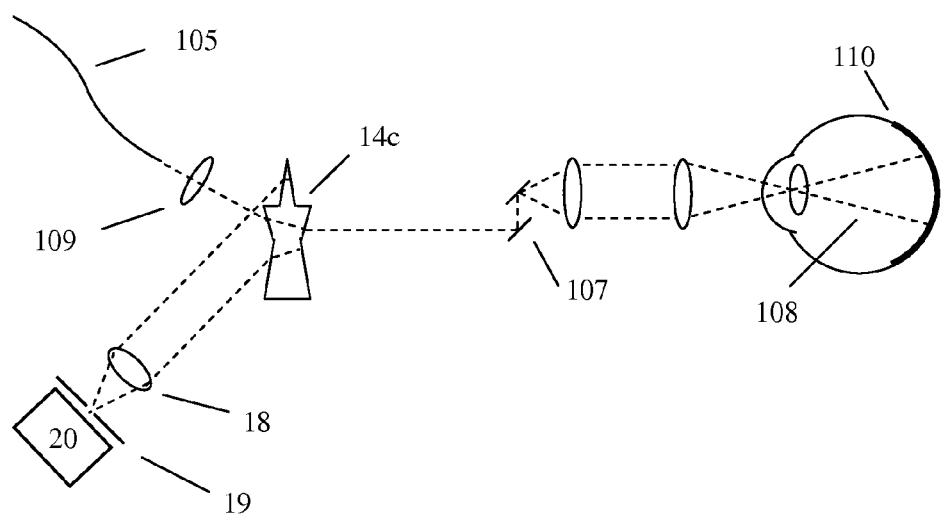
FIG. 3C is a diagram of an embodiment in which the OCT and CSLO signals are spatially decoupled by a wedged optic.

The OCT and CSLO signals may also be spatially decoupled in other ways. For example, they may be spatially decoupled using a mirror having two parts, each oriented at a different angle. The mirror may be configured such that when the returning sample beam reflects off the mirror, it splits into two components directed in different directions, one used to generate the OCT signal, and one used to generate the CSLO signal. In some embodiments, the second part of the mirror may radially surround the first part of the mirror. An example of such an embodiment is shown in FIG. 3B. It can also be accomplished by one or more wedged optics 14c that directs the two portions of the beam in different directions, as shown in FIG. 3C. A further possibility would be to use a dispersive component (a grating, for example) that directs the different signals in different directions based on their wavelengths. This approach would not rely on the spatial properties of the light reflected from the sample, but instead be based on the fact that the OCT and CSLO signals have different wavelength properties. The grating approach would only work if the desired OCT and CSLO signals have distinct wavelength bands. This could be useful if CSLO images of particular wavelengths were desired.

The present invention also allows for an additional improvement to the 2D confocal imaging performance by increasing the frame rate of confocal image generation by increasing the scan speed of the scanners. Current state-of-art OCT speed is constrained by the OCT data acquisition rate of the camera of 27 kHz, so a CSLO image generated during OCT scanning is limited by this rate. For a 200×200 fundus image the scan time is 1.48 seconds (200 pixels×200 pixels/27,000 pixels/second), and the refresh rate is 0.68 frames/seconds (1/1.48 seconds). When CSLO imaging is not constrained by OCT acquisition (i.e. OCT image acquisition is suspended), it is possible to operate at a data rate of 100,000 Hz until the fast-scan galvo reaches its mechanical limit of approximately 500 Hz (100,000 Hz/200 pixel). The same 200×200 fundus image would have a scan time of 0.4 seconds (200 pixels×200 pixels/100,000 pixels/second), and the refresh rate is 2 frames/seconds (1/0.4 seconds). This results in an increase in the frame rate of the 2D confocal image by a factor of four.

Although various embodiments that incorporate the teachings of the present invention have been shown and described in detail herein, those skilled in the art can readily devise other varied embodiments that still incorporate these teachings. In particular, any embodiment described with the separation of the CSLO and OCT components between the collimating lens and scanning elements could also be achieved with the separating element located between the collimating lens and fiber, and the reverse.

The following references are hereby incorporated by reference:

Patent Documents

U.S. Pat. No. 5,926,592 Harris et al. "Optical fibre confocal imager with variable near-confocal control"
U.S. Pat. No. 6,769,769 Podoleanu et al. "Optical mapping apparatus with adjustable depth resolution and multiple functionality"
U.S. Pat. No. 7,301,644 Knighton et al "Enhanced optical coherence tomography for anatomical mapping"
U.S. Pat. No. 7,382,464 Everett et al. "Apparatus and method for combined optical-coherence-tomographic and confocal detection"
U.S. Pat. No. 7,535,577 Podoleanu et al. "Optical mapping apparatus with optimized OCT configuration"
U.S. Pat. No. 7,649,629 Rogers et al. "Optical imaging apparatus with spectral detector"
US Patent Publication No. 2012/0218558 Cenko et al. "Apparatus and methods for optical coherence tomography and confocal microscopy"

Non-Patent Literature

Sharp, P. F. et al. (2004). "The scanning laser ophthalmoscope—a review of its role in bioscience and medicine." Physics in Medicine and Biology 49(7): 1085-1096
Fujimoto, J. G. et al. (2000). "Optical coherence tomography: an emerging technology for biomedical imaging and optical biopsy." Neoplasia 2(1-2): 9-25
Rollins, A. M. et al. (2002). "Emerging clinical applications of optical coherence tomography." Optics and Photonics News 13(4): 36-41
Fujimoto, J. G. (2003). "Optical coherence tomography for ultrahigh resolution in vivo imaging." Nature Biotechnology 21(11): 1361-1367
Podoleanu, A. G. et al. (1997). "Simultaneous en-face imaging of two layers in the human retina by low-coherence reflectometry." Optics Letters 22(13): 1039-1041
Podoleanu, A. G. et al. (1998). "En-face coherence imaging using galvanometer scanner modulation." Optics Letters 23(3): 147-149
A. G. Podoleanu et al. (1999). "Noise Analysis of a Combined Optical Coherence Tomograph and a Confocal Scanning Ophthalmoscope." Applied Optics 38(10): 2116-2127
A. G. Podoleanu et al. (2004). "Sequential optical coherence tomography and confocal imaging." Optics Letters 29(4): 364-366
Podoleanu et al. (2004). "Combined multiplanar optical coherence tomography and confocal scanning ophthalmoscopy," Journal of Biomedical Optics, 9(1): 86-93
Hitzenberger, C. K. et al. (2003). "Three-dimensional imaging of the human retina by high-speed optical coherence tomography." Optics Express 11(21): 2753-2761
Leitgeb, R. et al. (2004). "Ultrahigh resolution Fourier domain optical coherence tomography." Optics Express 12(10): 2156-2165

We claim:

1. A system for optical coherence tomography (OCT) and confocal scanning laser ophthalmoscopy (CSLO) comprising:
    a light source arranged to generate a beam of radiation;
    a beam divider for separating the beam along a sample arm and a reference arm;
    optics for scanning the beam in the sample arm over a set of transverse locations on a sample;
    a mirror located between the beam divider and the scanning optics, said mirror having a transmission region aligned with the axis of the sample beam, such that a first portion of the light returning from the sample is transmitted through the transmission region and a second portion of the light returning from the sample at locations radially outside the transmission region is reflected by the mirror;
    a first detector for measuring the first portion of the light returning from the sample and the radiation returning from the reference arm, and generating a first set of output signals in response thereto;
    a first processor for converting the first set of output signals into OCT image data;
    a second detector for measuring the second portion of the light returning from the sample, and generating a second set of output signals in response thereto; and
    a second processor for converting the second set of output signals into CSLO image data.

2. A system as recited in claim 1 wherein the transmission region is an aperture.

3. A system as recited in claim 1, wherein the transmission region is a transparent material.

4. A system as recited in claim 3, wherein the transparent material has an antireflective coating.

5. A system as recited in claim 1, further comprising a lens located between the mirror and the second detector for focusing the outer component of the light returning from the sample onto the second detector.

6. A system as recited in claim 1 wherein the transmission region is substantially circular.

7. A system as recited in claim 6, further comprising a collimating lens located along the path of the sample arm beam between the beam divider and the scanning optics,
    wherein the mirror is located along the path of the sample arm beam between the collimating lens and the sample.

8. A system as recited in claim 7, further comprising an optical fiber located between the mirror and the first detector for collecting light returning from the sample, the optical fiber having a numerical aperture (NA), and the collimating lens having focal length f,
    wherein the circular transmission region of the mirror has a diameter of at least 2*NA*f.

9. A system as recited in claim 6, further comprising a collimating lens located along the path of the sample arm beam between the beam divider and the scanning optics,
    wherein the mirror is located along the path of the sample arm beam between the collimating lens and the first detector.

10. A system as recited in claim 9, further comprising an optical fiber located between the mirror and the first detector for collecting light returning from the sample, the optical fiber having a numerical aperture (NA), wherein the circular transmission region of the mirror has a diameter of at least 2*NA*s, where s is the distance between the mirror and the optical fiber.

11. A system for optical coherence tomography (OCT) and confocal scanning laser ophthalmoscopy (CSLO) comprising:

a light source arranged to generate a beam of radiation;
a beam divider for separating the beam along a sample arm and a reference arm;
optics for scanning the beam in the sample arm over a set of transverse locations on a sample;
a reflective surface located between the beam divider and the scanning optics, the reflective surface having a circular shape aligned with the axis of the sample beam, such that a first portion of the light returning from the sample is reflected by the reflective surface, and a second portion of the light returning from the sample at locations radially outside the reflective surface is transmitted past the reflective surface;
a first detector for measuring the first portion of the light returning from the sample and the radiation returning from the reference arm, and generating a first set of output signals in response thereto;
a first processor for converting the first set of output signals into OCT image data;
a second detector for measuring the second portion of the light returning from the sample, and generating a second set of output signals in response thereto; and
a second processor for converting the second set of output signals into CSLO image data.

12. A system for optical coherence tomography (OCT) and confocal scanning laser ophthalmoscopy (CSLO) comprising:

a light source arranged to generate a beam of radiation;
a beam divider for separating the beam along a sample arm and a reference arm;
optics for scanning the beam in the sample arm over a set of transverse locations on a sample;
a reflective surface located between the beam divider and the scanning optics, the reflective surface having a first part and a second part, wherein the first part is aligned with the axis of the sample beam and is oriented at a different angle than the second part, such that a first portion of the light returning from the sample is reflected in one direction by the first part of the reflective surface, and a second portion of the light returning from the sample is reflected in a different direction by the second part of the reflective surface;
a first detector for measuring the first portion of the light returning from the sample and the radiation returning from the reference arm, and generating a first set of output signals in response thereto;
a first processor for converting the first set of output signals into OCT image data;
a second detector for measuring the second portion of the light returning from the sample, and generating a second set of output signals in response thereto; and
a second processor for converting the second set of output signals into CSLO image data.

* * * * *